United States Patent [19]

Barben, II

[11] 4,118,663
[45] Oct. 3, 1978

[54] FOUR ELECTRODE CONDUCTIVITY SENSOR

[75] Inventor: Theodore R. Barben, II, Carson City, Nev.

[73] Assignee: Thomas-Barben Instruments, Carson City, Nev.

[21] Appl. No.: 841,254

[22] Filed: Oct. 11, 1977

[51] Int. Cl.² .............................................. G01N 27/42
[52] U.S. Cl. .............................. 324/30 R; 204/195 R
[58] Field of Search ........... 204/195 R; 324/29, 30 R, 324/30 B, DIG. 1

[56] References Cited

U.S. PATENT DOCUMENTS

| 3,993,945 | 11/1976 | Watmoth | 324/30 B |
| 4,028,618 | 6/1977 | Teass, Jr. | 324/30 R |

Primary Examiner—M. Tokar
Attorney, Agent, or Firm—Nilsson, Robbins, Dalgarn, Berliner, Carson & Wurst

[57] ABSTRACT

In a four electrode conductivity sensor, each pair of electrodes is coupled to a respective one of two operational amplifier circuits that establish a fixed potential relationship between the two potential electrodes so that current flow between the two current electrodes is maintained directly proportional to the conductivity of the solution. Specifically a direct or alternating excitation voltage is applied to the positive input of one operational amplifier, while the other receives a fixed reference potential input. The operational amplifiers supply a unity gain, noninverted output to the respective current carrying electrodes, while the potential electrodes are directly connected to the feedback input of the respective amplifier. The current flow between the current electrodes is measured as a voltage signal across a resistor with the operational amplifier output and remains directly proportional to the conductivity of the solution in which the electrodes are immersed, regardless of fouling of the electrodes by solution impurities and electrolysis effects. An alternating current excitation input can be applied through a coupling capacitor with each electrode also connected through a coupling capacitor to provide direct current that eliminates ground loop problems in the installation and use of metering and control equipment.

10 Claims, 8 Drawing Figures

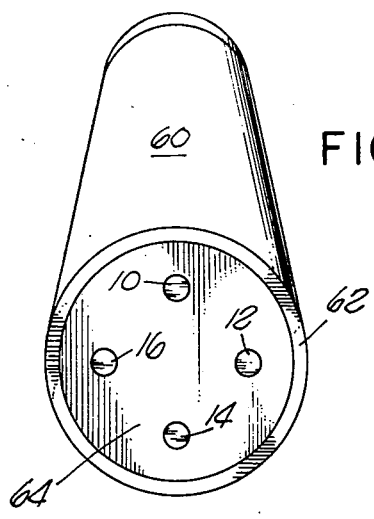
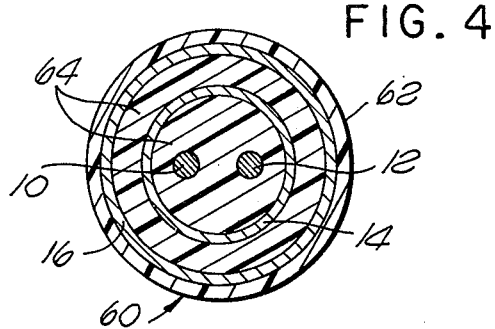
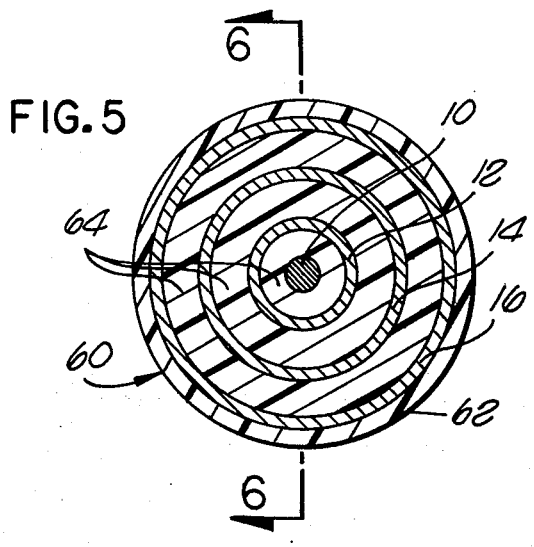
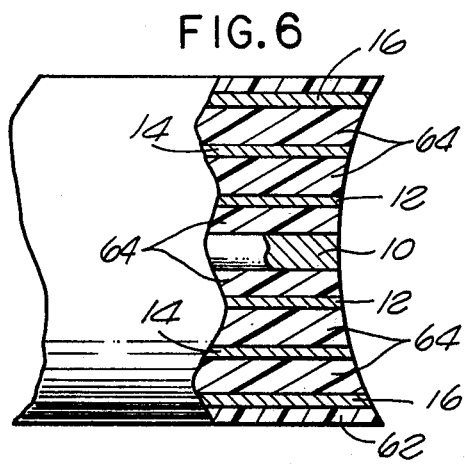
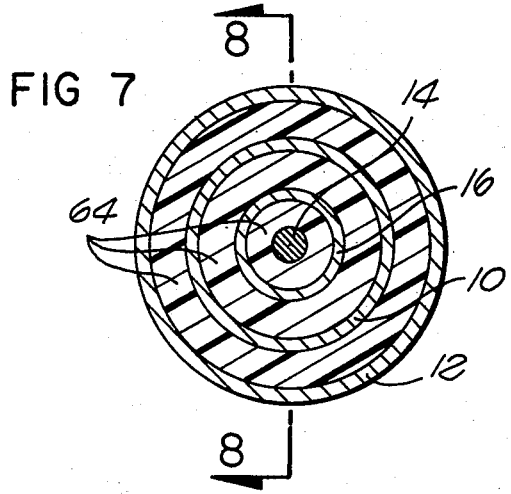
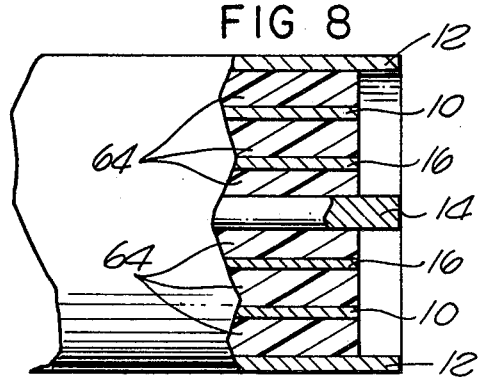

FOUR ELECTRODE CONDUCTIVITY SENSOR

BACKGROUND OF THE INVENTION

A. Field of the Invention

This invention relates to improved conductivity sensors of the type employed in recirculating water conditioning systems, such as disclosed in U.S. Pat. No. 3,361,150 issued Jan. 2, 1968 to J. E. Horner where fresh feed water is added to the system to limit the concentration of dissolved solids.

B. Prior Art

In most systems, the conductivity of a solution is monitored using either of two basic methods. One measures conductivity directly by maintaining a fixed voltage between electrodes immersed in solution so that the resulting current flow is directly proportional to the conductivity. Conversely, the electrodes may be supplied with a constant current flow so that the potential between them is directly proportional to the resistivity of the solution, which is the reciprocal of its conductivity.

In many applications, a simple two electrode system has sufficed. As pointed out in the aforementioned Horner patent, the application of an alternating current excitation is preferred for continuous monitoring to prevent the corrosion and buildup of electrolysis products at the electrode surface interface with the solution. Nevertheless, in many process streams, such as those employing cooling water evaporation for air-conditioning systems for commercial and industrial buildings, solid impurities carried by the stream are deposited upon the electrode surfaces. Over extended periods of use, the fouling of the electrodes by the buildup of these impurities can introduce a substantial impedance across the interface between the electrode metal and the solution, thus spoiling the accuracy of the conductivity reading by indicating a much lower value than is actually present in the solution itself. Since such a result could have serious consequences for the entire recirculation system, operation had to be periodically interrupted to permit inspection and cleaning of these electrodes to insure proper response.

More recently, various four electrode conductivity monitoring systems have been developed to alleviate these problems. In these arrangements, two electrodes are coupled through a high impedance circuit to determine a potential relationship, whereas a relatively low impedance constant current source supplies the other two. With the impedance in the voltage circuit much higher than the interface resistance between the electrode and the solution due to fouling or corrosion, the existing potential is primarily due to the voltage drop produced by the current flow through the solution between the other two electrodes. By holding the current constant between those electrodes, the measured voltage between the other two is then directly proportional to the resistivity of the solution, even with considerable fouling by impurities and corrosion products. However, in order to produce an output signal proportional to conductivity, an electronic reciprocal generator with its inherent cost and inaccuracy is needed to convert the resistivity signal.

Also, as explained in the aforementioned patent, the voltage between most metal electrodes should not exceed their free corroding potential, typically about 40 millivolts, so as to not foreshorten their usable life. On the other hand maximum signal strength decreases the noise effects of stray currents and the like to make the measurements more precise. Therefore, the voltage produced by a constant current might exceed permissable corrosion potential limits when the electrodes become fouled unless the initial operating levels are set well below permissable limits, thus decreasing the available signal-to-noise ratio.

SUMMARY OF THE INVENTION

This invention involves operational amplifier circuits for measuring solution conductivity directly using a variety of four electrode configurations wherein a predetermined excitation voltage is maintained between two of the electrodes, while current flow between the other two is measured as directly proportional to the conductivity of the solution. The circuit employs two operational amplifiers, each operating in a unity gain, non-inverting mode with its output connected through a respective one of a pair of current electrodes. One of the operational amplifiers receives a predetermined excitation voltage input, whereas the input of the other is coupled to a common or ground reference potential. The other pair of electrodes are potential electrodes, each connected directly to the high impedance feedback input of a respective operational amplifier. By this means, the potential at the solution interface of the respective current carrying electrodes is maintained at the predetermined input level, and the current flow between the current electrodes can be monitored as the voltage developed across a resistor connected in series with the amplifier output which is directly proportional to the conductivity of the solution.

In the preferred embodiment, the excitation voltage is supplied to the noninverting or positive input of one operational amplifier from a regulated alternating current source, whereas a reference ground potential is applied to the noninverting input of the other operational amplifier. With the alternating current voltage excitation, direct current isolation can be achieved between the conductivity electrode and the output signal to eliminate ground loop couplings through the recorder, controller or other output equipment, thus permitting its easy and quick installation and calibration. This isolation is accomplished merely by applying the alternating current excitation voltage to the respective operational amplifier input through a capacitive coupling and using a similar capacitive coupling between the amplifiers and each of the electrodes. The circuit automatically compensates for this capacitive coupling impedance in the same manner as for the varying interface impedance due to electrode fouling.

The electrodes may be arranged in line with one another, preferably with the current electrodes adjacent each other between the respective potential electrodes. Also the four electrodes may be assembled together in a unitary probe structure with individual electrodes separated and held in place by insulating material. In one such probe configuration, the electrodes consist of four metallic rods located at right angles to one another with equal radial displacement from the central axis of a cylindrical probe body and encapsulated with a suitable epoxy filling or potting compound. Another desirable probe configuration has a central rod electrode surrounded by two concentric tubular metal tube electrodes within a cylindrical metal probe housing that serves as the final electrode with an epoxy or potting compound filling the intervening spaces. Another variation employs three concentric metal tube electrodes surrounding a central rod within a plastic or other insulative probe housing, and the end surface in contact with the solution may be concave so that the ends of the tubular electrodes are progressively recessed to avoid short circuiting of the conductive path through the solution between the adjacent current electrodes, that also have larger exposed surfaces to better resist fouling. For higher excitation voltages, the central rod and outer tubular electrodes may protrude outward from the body of the probe to serve as the current electrodes so that the added exposed area reduces current density.

BRIEF DESCRIPTION OF THE DRAWINGS

FIG. 3 is a perspective view of a four electrode probe assembly showing the arrangement of four metal rods for use in the system of the invention;

FIG. 4 is a front elevational view of another integral electrode probe assembly with two centrally disposed rods combined with two concentric tubular metal electrodes;

FIG. 5 is a front elevational view of a further form of integral probe assembly for use with the system of the invention employing a central metal rod with concentric tubular metal electrodes within a probe housing;

FIG. 6 is a partial cross-sectional view taken along the line 6—6 of the probe assembly in FIG. 5 illustrating a preferred concave front surface configuration;

FIG. 7 is a front elevational view of yet another alternative probe assembly configuration involving a central metal rod with concentric tubular metal electrodes, the outer of which comprises the probe assembly housing for achieving a stable ground reference in certain application; and, FIG. 8 is a partial cross-sectional view of the probe assembly of FIG. 7 taken along the lines 8—8 showing a special electrode configuration with the center and outer current electrodes protruding beyond the others for use in precision measurement with higher excitation voltages or for low conductivity solutions.

DETAILED DESCRIPTION

Figure 1:
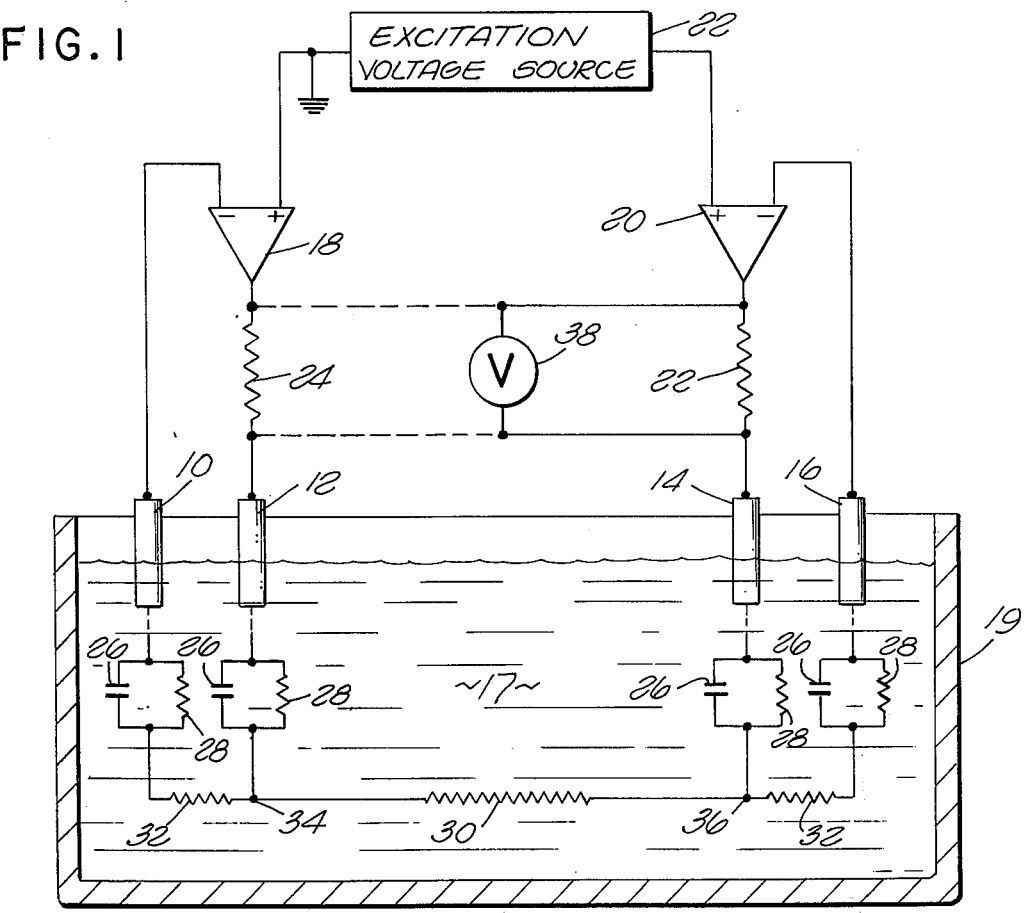
FIG. 1 is a generalized schematic circuit diagram of the conductivity metering system in accordance with the invention, including an equivalent circuit illustration of the impedance relationship between electrodes in the test solution.

Referring now to FIG. 1, which is a generalized circuit schematic of the system, four electrodes 10, 12, 14, and 16 are shown immersed in a sample solution 17 within a container 19. The sample solution 17 is typically a sample stream taken from the main recirculation loop of an evaporative cooling or steam boiler feed system wherein conductivity is measured to control drainage of the existing flow for replacement with fresh water to prevent the buildup of excessive dissolved solids. Thus, the container 19 represents the pipe or cavity walls for the sample stream diverted from the main stream for monitoring purposes.

The electrodes 10, 12, 14 and 16 are shown in a simple in-line arrangement with the outermost electrodes 10 and 16 being the potential electrodes and the two adjacent inner electrodes 12 and 14 being the current electrodes in the four electrode system. However, the positions of these electrodes can generally be interchanged without significant effect, except that under special circumstances as hereinafter described.

The electrodes 10, 12, 14 and 16 are selectively coupled to a pair of operational amplifiers 18 and 20. The operational amplifier 18 controls the potential signal and current flow for the two ground electrodes 10 and 12 that operate a common base reference or ground potential. The signal electrodes 14 and 16 have their respective current flow and potential determined by the impact signal to the operational amplifier 20 from an excitation voltage source 22. Both of the operational amplifiers 18 and 20 are connected to operate in a non-inverting, substantially unity gain mode.

In the particular example illustrated, the ground or base reference potential is applied to the positive or non-inverting input of the operational amplifier 18, and its output is coupled through a series resistor 22 to the associated current electrode 12. The potential electrode 10 of that pair is coupled directly to the negative or inverting feedback terminal of the operational amplifier 18, which serves to maintain it at precisely the same potential level aplied to the other amplifier input, as more fully explained hereinafter.

Similarly, an excitation voltage signal from the source 22, which in this example is a regulated direct current voltage, is applied to the positive or non-inverting input of the operational amplifier 20 that has its output coupled directly through a series output resistor 24 to the associated current electrode 14, whereas the associated potential electrode 16 is coupled to the negative or inverting feedback input to be maintained at precisely the same potential level as the excitation voltage applied to the positive input.

An equivalent circuit is shown below the electrodes 10, 12, 14 and 16 connected by dashed lines to indicate the electrical properties of the electrical interface coupling into and through the solution between electrodes. The interface between each electrode and the surrounding solution is shown as an equivalent network of a capacitor 26 in parallel with a resistance 28. Although the equivalent capacitive and resistive element for each electrode are identically represented with the same reference numerals, the actual values may vary between electrodes depending upon the type and thickness of the impurities deposited on the electrode surface and the possible buildup of oxidation products. For example, because of the current flow between the resistors 12 and 14, the buildup of oxidation products and certain impurities would be greater than for the potential electrodes 10 and 16. Also, with a direct current excitation, certain ions would be plated onto one or the other set of electrodes depending on the polarity. On the other hand, the resistor 30 represents the equivalent resistive value in the path through the solution between the current carrying electrodes 12 and 14, and thus corresponds to the solution characteristic being measured. Likewise, the resistors 32 represent the path through the solution between the corresponding pairs of potential and current electrodes 10 and 12 and 16 and 14.

As those familar with the general characteristics of operational amplifiers recognize, the input impedance is extremely high, in the order of a megohm or more with field effect transistor (FET) elements differentially connected as the active amplifier components. Such amplifiers also exhibit a very high internal gain capability so that the output is adjusted to provide a negative feedback voltage signal at the negative or inverting input to precisely balance the voltage signal applied at the positive or noninverting input. Thus, in the system illustrated in FIG. 1 the output from the operational amplifier 18 produces a feedback voltage at the node 34, which represents the point of solution contact with the interface for the electrode 12. This feedback voltage is applied through a feedback network consisting of the equivalent solution resistance 32, the equivalent capacitive-resistive interface impedance elements 26 and 28, and the electrode body 10 directly to the negative or inverting amplifier input. With the amplifier input impedance so great compared to the solution and electrode interface equivalent resistances 32 and 28, virtually no current flows in the feedback path, and thus no voltage drop occurs between the nodal point 34 and the negative amplifier input. Thus the ground or reference potential applied to the positive amplifier input is maintained where the solution contacts the outer surface of the current carrying electrode 12.

Similarly, there is virtually no feedback current flow through the corresponding equivalent solution and interface elements 32, 26 and 28 and potential electrode 16 to the negative input terminal of the other operational amplifier 20 so that its output maintains nodal point 36, which represents the point of solution contact with the interface on the current electrode 14, at precisely the level of the excitation voltage applied to the positive amplifier input. Therefore, assuming a fixed positive voltage excitation applied to the input of the operational amplifier 20, current flows from its output to the output of the operational amplifier 18 so that the current flow across the solution resistance 30 is held precisely at the level necessary to match the excitation voltage level. This current flow is monitored by a voltage meter 38 across a resistor 22 or 24 connected in series with the output of either of the operational amplifiers 18 or 20 to provide a precise direct measure of the conductivity level within the solution.

A refined version of the four electrode system of FIG. 1, which is preferred in most installations, incorporates an alternating current excitation that permits direct isolation of the components to prevent ground loop problems in the installation and calibration of associated control circuitry. The alternating current excitation is obtained from a regulated square or sine wave generator 22', which may be of any conventional design, but preferably an integrated function generator such as the Intersil 8038CC with external components coupled to provide a sine wave output at a frequency of 1 kilohertz. The alternating excitation current is applied through an direct current isolating capacitor 40 of about 1 microfarad and an input resistor 42 to the positive noninverting input of the operational amplifier 20, typically of the type bearing the product designation 1/4 LM348N. The input voltage is developed across a resistor 44, which may be coupled in series with an appropriate resistive element of an external temperature compensation circuit connected across the terminals in place of the illustrated bridging element 46. The proportion of the total output signal strength from the regulated sine wave generator 22', which may be as high as 20 or more volts peak to peak, is determined by the ratio of the total impedance of the series connected elements 44 and 46 to the combined impedance including the input resistor 42 and coupling capacitor 40.

The excitation output from the operational amplifier 20 is coupled through an output resistor 22, typically 1 kilohm, and a direct current isolating capacitor 48 of about 1 microfarad to the current carrying electrode 14.

The associated potential electrode 16 is similarly coupled through a direct current isolating capacitor 50 of similar value to the negative inverting input of the operational amplifier 20. For stability, the amplifier output is coupled to the feedback circuit through a very high impedance resistor 52 of about 1 megohm.

The positive noninverting input of the operational amplifier 18 is coupled to ground potential through an input resistor 54, typically about 3 kilohms, and its output is coupled through another 1 microfarad isolation capacitor 52 to the current carrying electrode 12. The potential electrode 10 is similarly connected to a direct current isolation capacitor 54 to provide negative feedback to the negative inverting terminal of the amplifier 18. A high valued resistor 56 in the order of 1 megohm couples the amplifier output to negative inverting input terminal for stability. The system output signal developed across the resistor 22 is applied to an output amplifier and meter control circuit 38'. Typically, this may consist of additional amplifier stages and conversion or rectifier circuitry for developing specific control signals for recording conductivity levels and actuating solenoid operated controls for draining a portion of the circulating stream and replacing it with fresh feed water.

By reason of the direct current isolation provided by the coupling capacitor 40, 48, 50, 52 and 54, the conductivity sensing circuitry is effectively isolated from direct current ground loop that might be established through the recirculation piping to the exterior control circuitry so that installation and calibration can be made without precise adjustment and calibration to compensate for these loops. System calibration can instead be simply accomplished by closing the switch 58 to connect the excitation output from the operational amplifier 20 through the output resistor 22 to the output of the ground operational amplifier 18 to produce a fixed voltage drop across the output resistor 22. It is noted that the added impedance of the coupling capacitors 48, 50, 52 and 54 are compensated by the same mechanism that compensates for the interface impedance existing at the electrode surfaces.

Figure 2:
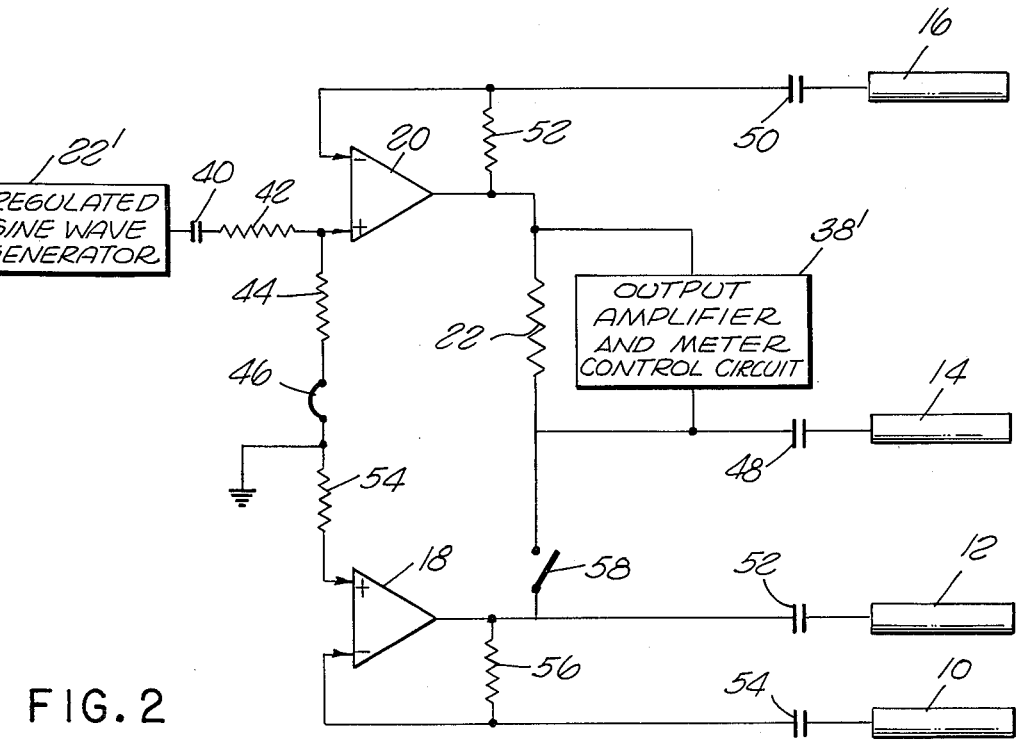
FIG. 2 is a more detailed schematic circuit diagram of a preferred form of the system in accordance with the invention that includes direct current isolation for eliminating ground loops.

Referring now to FIGS. 3 through 8, various alternative probe arrangements are shown for use in different applications in place of the basin in-line electrode arrangement illustrated in connection with FIGS. 1 and 2. In FIG. 3, the four electrodes 10, 12, 14 and 16 each consist of a metal rod extending longitudinally within an elongated cylindrical probe body 60. The probe body may consist of a cylindrical outer housing 62 of plastic or some other insulating material, which may also have its end threaded to fit into a threaded opening in the sample stream chamber. The electrode rods 10, 12, 14 and 16 are disposed parallel to one another within the housing 62 at right angles from one another and equally displaced from the longitudinal axis. The housing 62 is then filled to the desired depth with an epoxy potting compound 64 or the like that holds the rods in position. With low voltage excitation, which may typically be as little as 3 millivolts, only the ends of the rods need by exposed as shown, but the length of the rods can either be extended or the depth of the insulation compound 64 reduced to expose more of the rod length for higher excitation voltages or to allow higher currents to flow with the same excitation voltages in low conductivity solutions.

In FIG. 4, a probe arrangement is shown wherein one pair of electrodes 10 and 12 are centrally disposed metal rods extending longitudinally within the cylindrical probe housing 62 displaced a short distance on either side of the central axis. The other pair of electrodes 14 and 16 are implemented as concentric metal tubes extending longitudinally to surround the central rods 10 and 12 with the insulation compound filling the intervening spaces.

Similarly, in FIG. 5 the central pair of electrodes 10 and 12 consist of a solid metal rod 10 extending along the central axis with a concentric small metal tube for the electrode 12. The other pair of electrodes 14 and 16 are progressively larger metal tubes with the epoxy potting compound filling the intervening spaces. The advantages of the concentric tube configuration employed in the probe embodiments of FIGS. 4 and 5 is found in the larger contact surface area of the tubular electrodes for higher excitation levels and the greater distance between electrodes to increase solution resistance 30 when measuring high conductivity solutions. For example, in FIG. 4, the tubular electrode 14 might serve as a current carrying electrode in a system using a direct current excitation wherein a certain impurity or ion is deposited by the existing polarity on one current electrode so that the larger surface contact area serves to distribute the total deposits to prevent the coating from building up too quickly. In FIG. 5, the use of tubular current carrying electrodes 12 and 14 provides a larger surface area for both polarities than might be used for an alternating current excitation.

In FIG. 6, the tubular electrode arrangement of FIG. 5 is further provided with a concavely shaped end surface for contact with the test solution. In this arrangement, the contact surface areas of the electrodes is increased slightly by the amount of the curve. and the electrodes themselves are somewhat recessed from the path of flow to reduce the rate of deposits from the passing sample stream.

Finally, in FIG. 7 a probe arrangement is shown wherein the outer plastic housing 62 is eliminated so that the probe housing is defined by a tubular metal electrode 12, which serves as the current carrying electrode from the common reference or ground electrode pair. This outer metal electrode can thus be maintained in direct contact with the piping system of the boiler or recirculating water cooling system to establish a high capacity ground contact for high precision systems employing elevated energy excitation levels. As seen in a partial cross-sectional view of FIG. 8, the outer and center current carrying electrodes 12 and 14 are extended outwardly beyond the adjacent potential electrtodes 10 and 16 to provide much greater contact area with the solution. For precision conductivity measurements, or for measuring very low conductivity solutions, the level of the alternating current excitation voltage input has been as high as 10 volts (20 volts peak to peak) and the greater contact area reduces the rate of buildup of oxidation products. Moreover, in such instances, a low corrosion material is employed such as stainless steel electrodes with an ASI rating of 316 to reduce corrosion effects.

Whereas specific circuitry and electrode probe arrangements have been illustrated and described herein in order to indicate preferred embodiments of the invention, it should be understood that various other arrangements may be employed without departing from the spirit and scope of the invention as defined in the appended claims.

I claim:

1. In a four electrode conductivity sensor having opposing pairs of potential and current electrodes, the control and measuring system comprising:
   first and second operational amplifiers each having inverting and noninverting inputs and an output coupled to a respective one of said current electrodes;
   grounding means for applying a common reference potential to the noninverting input of said first operational amplifier;
   voltage source means for applying a regulated excitation potential to the noninverting input of said second operational amplifier;
   first and second feedback means coupling the associated potential electrode of each opposing pair directly to the inverting input of the respective first and second operational amplifiers;
   means for immersing the opposing pairs of potential and current electrodes in fixed relative positions within a solution having its conductivity measured whereby the impedance in the feedback path to the inverting input of both operational amplifiers from said potential electrode greatly exceeds the impedance within the solution betw-en electrodes; and,
   output circuit means including an output resistance element coupled in series with the output of one of said operational amplifiers to produce an output voltage proportional to the current flow between said current electrodes directly proportional to the conductivity of the solution between said electrodes.

2. The four electrode conductivity sensor system of claim 1 wherein:
   said voltage source means consist of a regulated sine wave generator for applying a fixed amplitude alternating current signal to the noninverting input of said second operational amplifier.

3. The four electrode conductivity sensor system of claim 2 wherein:
   said fixed amplitude alternating current signal has a frequency of about 1 kilohertz.

4. The four electrode conductivity sensor system of claim 2 wherein:
   said voltage source means is coupled to the noninverting input of said second operational amplifier through a coupling capacitor; and,
   each of said potential and current electrodes are coupled to its respective inverting input and output of said operational amplifiers through a coupling capacitor of approximately the same capacitive value, whereby the operation of said amplifiers is isolated from direct current ground loops.

5. The four electrode conductivity sensor system in accordance with claim 1 wherein:
   said means for immersing the opposing pairs of potential and current electrodes in fixed relative positions includes an elongated probe assembly wherein each of said electrodes is in the form of a metal rod extending longitudinally parallel to the central axis and displaced equidistant therefrom at right angles to one another, and an insulative potting compound filling the interior of said probe assembly between said rods.

6. The four electrode conductivity sensor system of claim 1 wherein:
   said means for immersing the opposing pairs of potential and current electrodes includes an elongated probe assembly having one opposing pair of potential and current electrodes consisting of a pair of elongated metal rods disposed adjacent one another on either side of the central axis of said probe assembly and a pair of concentric tubular metal cylinders surrounding said metal rods constituting the other opposing pair of potential and current electrodes, and an insulative potting compound filling the spaces between said metal cylinders and said rods.

7. The four electrode conductivity sensor system of claim 1 wherein:

said means for immersing the opposing pairs of potential and current electrodes in fixed relative position includes an elongated probe housing with one of said potential electrodes consisting of an elongated metal rod extending along the central axis of said probe housing, and three concentric tubular metal cylinders surrounding said rod with an insultative potting compound filling the spaces between said rod and each of the adjacent cylinders.

8. The four electrode conductivity sensor system of claim 7 wherein:

the outermost of said cylinders constitutes said other potential electrode, and the transverse face of said probe assembly exposed to said solution is concave so that the inwardly sloped end surfaces of said cylinders have a greater metal surface area exposed to said solution and a greater distance between electrodes.

9. The four electrode conductivity sensor system of claim 1 wherein:

said means for immersing said opposing pairs of potential and current electrodes in fixed relative positions includes an elongated probe assembly with one of said current electrodes consisting of a solid metal rod extending along the central axis of said probe assembly and three concentric metal cylinders surrounding said metal rod, the outermost of said cylinders defining the outer surface of said probe assembly and constituting the current electrode coupled to the output of said first operational amplifier with an insulative potting compound filling the intervening spaces between said rod and each of said concentric metal cylinders.

10. The four electrode conductivity sensor of claim 9 wherein:

said rod and said outermost metal cylinder extend longitudinally outward beyond the immersed end surfaces of the two intermediate metal cylinders to provide a greater metal surface area immersed in said solution.

* * * * *

UNITED STATES PATENT AND TRADEMARK OFFICE
CERTIFICATE OF CORRECTION

PATENT NO. : 4,118,663
DATED : October 3, 1978
INVENTOR(S) : THEODORE R. BARBEN, II It is certified that error appears in the above-identified patent and that said Letters Patent are hereby corrected as shown below:

In the abstract, third line from the bottom, after "current" insert --isolation--.

In column 5, Line 17; insert after "outer" --interface-- .

In column 7, line 34; "." should be --,--.

Signed and Sealed this

Seventeenth Day of April 1979

[SEAL]

Attest:

RUTH C. MASON
Attesting Officer

DONALD W. BANNER
Commissioner of Patents and Trademarks